(12) United States Patent
Swaile et al.

(10) Patent No.: US 9,149,662 B2
(45) Date of Patent: Oct. 6, 2015

(54) METHOD FOR MAKING AN EMULSIFIED ANTIPERSPIRANT PRODUCT

(75) Inventors: David Frederick Swaile, Cincinnati, OH (US); Gary Paul Shrum, Maineville, OH (US); David Arthur Sturgis, Cincinnati, OH (US); Songtao Zhou, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/140,891

(22) Filed: Jun. 17, 2008

(65) Prior Publication Data

US 2009/0269292 A1    Oct. 29, 2009

Related U.S. Application Data

(60) Provisional application No. 60/936,100, filed on Jun. 18, 2007.

(51) Int. Cl.
*A61K 8/00* (2006.01)
*A61Q 15/00* (2006.01)
*A61K 8/06* (2006.01)

(52) U.S. Cl.
CPC . *A61Q 15/00* (2013.01); *A61K 8/06* (2013.01); *A61K 8/064* (2013.01)

(58) Field of Classification Search
CPC .......... A61Q 15/00; A61K 8/06; A61K 8/064
See application file for complete search history.

(56) References Cited

U.S. PATENT DOCUMENTS

| | | | |
|---|---|---|---|
| 4,948,578 A | 8/1990 | Burger et al. | |
| 5,500,209 A | 3/1996 | Ross et al. | |
| 5,603,925 A | 2/1997 | Ross et al. | |
| 5,871,720 A | 2/1999 | Gutierrez et al. | |
| 5,891,425 A | 4/1999 | Bretzler et al. | |
| 6,033,651 A | 3/2000 | Dolak et al. | |
| 6,171,581 B1 | 1/2001 | Joshi et al. | |
| 6,187,842 B1 | 2/2001 | Kobayashi et al. | |
| 6,231,841 B1 | 5/2001 | Franklin et al. | |
| 6,241,976 B1 | 6/2001 | Esser et al. | |
| 6,245,325 B1 | 6/2001 | Shen | |
| 6,248,312 B1 | 6/2001 | Franklin et al. | |
| 6,251,377 B1 | 6/2001 | Franklin | |
| 6,287,544 B1 * | 9/2001 | Franklin et al. | 424/65 |
| 6,338,840 B1 | 1/2002 | Allan et al. | |
| 6,338,841 B1 | 1/2002 | Mattai et al. | |
| 6,338,858 B1 | 1/2002 | Dupuis et al. | |
| 6,451,295 B1 | 9/2002 | Cai et al. | |
| 6,458,345 B1 | 10/2002 | Emslie et al. | |
| 6,589,515 B2 | 7/2003 | Franklin et al. | |
| 6,680,048 B2 | 1/2004 | Grainger et al. | |
| 6,703,005 B2 | 3/2004 | Allan et al. | |
| 6,749,841 B2 | 6/2004 | Joshi et al. | |
| 6,942,850 B2 | 9/2005 | Coe et al. | |
| 7,083,800 B1 | 8/2006 | Terren et al. | |
| 7,329,403 B2 | 2/2008 | Chuah et al. | |
| 7,347,990 B2 | 3/2008 | Emslie et al. | |
| 2004/0167231 A1 | 8/2004 | Kawagoe | |
| 2005/0191254 A1 | 9/2005 | Walling et al. | |
| 2006/0051306 A1 | 3/2006 | Brown et al. | |
| 2006/0115441 A1 * | 6/2006 | James et al. | 424/66 |
| 2008/0063616 A1 | 3/2008 | Walling et al. | |

FOREIGN PATENT DOCUMENTS

| | | |
|---|---|---|
| DE | 10210461 A1 | 9/2003 |
| EP | 0 295 071 A2 | 12/1988 |
| EP | 0 930 868 B1 | 7/1999 |
| EP | 1 076 551 B1 | 7/2002 |
| WO | WO 98/24404 | 6/1998 |

OTHER PUBLICATIONS

U.S. Appl. No. 12/140,853, filed Jun. 17, 2008, David Frederick Swaile, et al.
International Search Report PCT/IB2008/052406 with Written Opinion of the International Searching Authority, mailing date Jan. 4, 2010, 11 pages.

* cited by examiner

*Primary Examiner* — Johann R Richter
*Assistant Examiner* — David Browe

(57) ABSTRACT

Methods for making antiperspirant products in the form of emulsions are provided, wherein the emulsion comprises a continuous water-immiscible phase and a disperse aqueous phase comprising an antiperspirant active. The method comprises the steps of providing a water-immiscible liquid, providing an aqueous solution comprising an antiperspirant active, preparing an emulsion comprising a continuous phase including the water-immiscible liquid and a disperse phase including the aqueous solution, heating the emulsion to a temperature between about 60° C. and about 110° C., providing a structurant that is at least partially dissolved, adding the heated emulsion to the at least partially dissolved structurant to form an emulsified antiperspirant composition, and transferring the emulsified antiperspirant into a dispensing container within about 2 hours of initiating the heating step.

16 Claims, 3 Drawing Sheets

METHOD FOR MAKING AN EMULSIFIED ANTIPERSPIRANT PRODUCT

CROSS REFERENCE TO RELATED APPLICATION

This application claims the benefit under 35 USC 119(e) to U.S. Application No. 60/936,100, filed Jun. 18, 2007.

FIELD OF THE INVENTION

The present invention is directed to methods for making antiperspirant products that are in the form of emulsions comprising a continuous water-immiscible phase and a disperse aqueous phase.

BACKGROUND OF THE INVENTION

Antiperspirant products can be considered drugs, and as such, their active level must be within 10% of the active weight indicated on the product packaging. Thus, the making process must assure that there is no loss of volatiles that would increase the active level. This is particularly difficult for multi-phase products having an interior (disperse) aqueous phase that can evaporate through the external (continuous) phase, such as a water-in silicone oil emulsion. Any evaporated water that condenses but is maintained with the product can find itself in the wrong phase of the product, which may break the emulsion or result in product syneresis. Accordingly, there is room in the art for improvement.

DETAILED DESCRIPTION OF THE INVENTION

Figure 1:
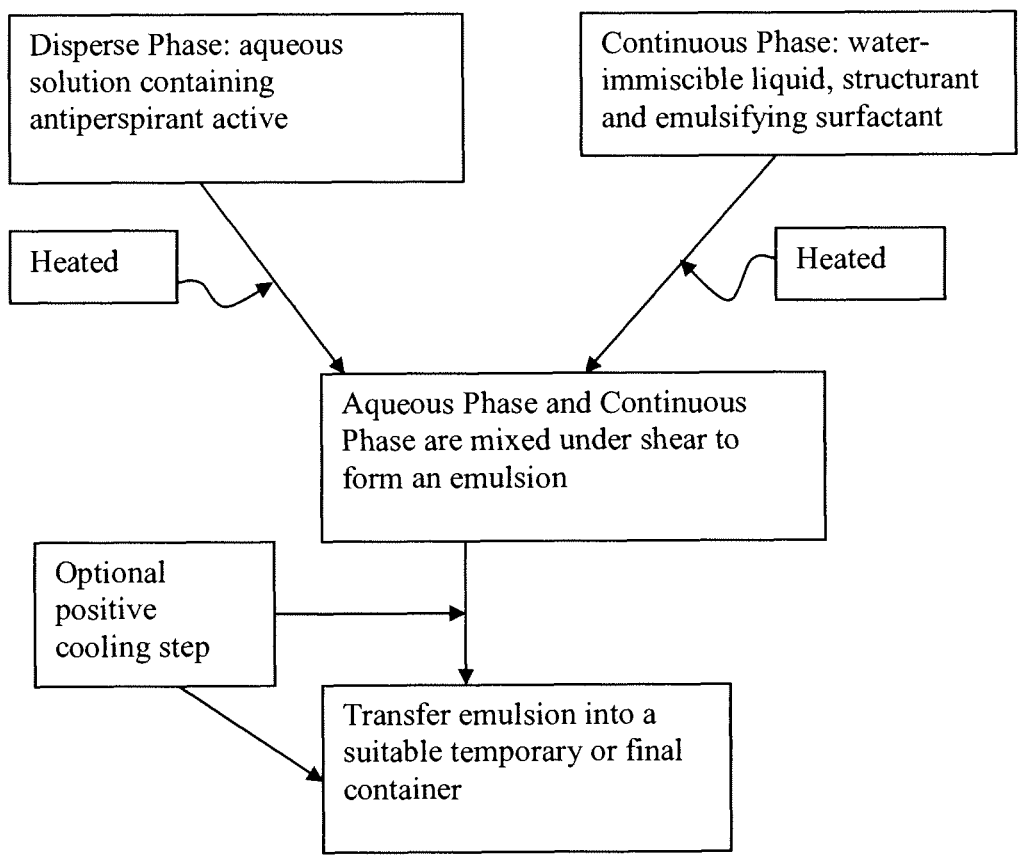
FIG. 1 is a schematic of a first exemplary method for making antiperspirant products.

The present invention may be understood more readily by reference to the following detailed description of illustrative and preferred embodiments. It is to be understood that the scope of the claims is not limited to the specific ingredients, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

All percentages and ratios used herein are by weight of the total composition, and all measurements made are at 25° C., unless otherwise designated.

The compositions/methods of the present invention can comprise, consist of, and consist essentially of the features and/or steps of the invention described herein, as well as any of the additional or optional ingredients, components, steps, or limitations described herein.

The term "ambient conditions" as used herein refers to surrounding conditions at about one atmosphere of pressure, about 50% relative humidity and about 25° C.

The term "water-immiscible" as used herein refers to materials or mixtures of materials with less than 1% water solubility at 25° C., and preferably less than 0.1% water solubility at 25° C. Most preferable are materials with less than 0.01% water solubility at 25° C.

The term "volatile" as used herein refers to those materials which have a measurable vapor pressure as measured at 25° C. and 1 atmosphere. The term "moderately volatile material," as used herein, refers to those materials with a vapor pressure below about 2 mmHg at 25° C. The term "low volatile material," as used herein, refers to those materials with a vapor pressure below about 0.5 mmHg at 25° C. The term "nonvolatile material," as used herein, refers to those materials with a vapor pressure below about 0.002 mmHg at 25° C. Vapor pressures can be measured in a variety of manners and are often available in a variety of chemical data bases that would be known to one skilled in the art. One such database is available from the Research Institute for Fragrance Materials.

The present invention is directed to methods for making emulsified antiperspirant products that comprise a continuous phase and a disperse aqueous phase. The continuous phase includes one or more water-immiscible liquids and a structurant. And the disperse phase includes a solution of antiperspirant active in water. Compositional features of antiperspirant products that may be manufactured by methods according to the present invention will be discussed first, followed by a detailed discussion of exemplary method embodiments.

I. Continuous Phase

A. Water-Immiscible Liquid

The concentration of the water-immiscible liquid preferably ranges from about 10% to about 30%, by weight of the composition. Other concentrations however are also contemplated herein.

One preferred water-immiscible liquid that may be employed in exemplary antiperspirant compositions that can be made in accordance with the present invention comprises volatile silicones, non-volatile silicones, or mixtures of these materials. Nonlimiting examples include those volatile silicones that are described in Todd et al., "Volatile Silicone Fluids for Cosmetics", Cosmetics and Toiletries, 91:27-32 (1976). Suitable amongst these volatile silicones include the cyclic silicones having from about 3 or from about 4 to about 7 or to about 6, silicon atoms. Specifically are those which conform to the formula:

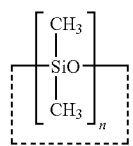

wherein n is from about 3, from about 4 or about 5 to about 7 or to about 6. These volatile cyclic silicones generally have a viscosity value of less than about 10 centistokes. Other suitable water-immiscible liquids for use herein include those volatile and nonvolatile linear silicones which conform to the formula:

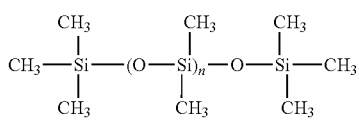

wherein n is greater than or equal to 0. The volatile linear silicone materials will generally have viscosity values of less than 5 centistokes at 25° C. The non-volatile linear silicone materials will generally have viscosity values of greater than 5 centistokes at 25° C.

Specific examples of suitable volatile silicones for use herein include, but are not limited to, hexamethyldisiloxane; Silicone Fluids SF-1202 and SF-1173 (commercially available from G.E. Silicones); Dow Corning 244, Dow Corning 245, Dow Corning 246, Dow Corning 344, and Dow Corning 345, (commercially available from Dow Corning Corp.); Silicone Fluids SWS-03314, SWS-03400, F-222, F-223, F-250, and F-251 (commercially available from SWS Silicones Corp.); Volatile Silicones 7158, 7207, 7349 (available from Union Carbide); Masil SF-V™ (available from Mazer); and mixtures thereof. Examples of preferred volatile silicones include cyclohexamethylsiloxane, hexyl methicone, capryl methicone and linear or branched polydimethyl siloxanes containing 4 to 6 silicone atoms.

Specific examples of suitable non-volatile linear silicones for use herein include, but are not limited to, Rhodorsil Oils 70047 available from Rhone-Poulenc; Masil SF Fluid available from Mazer; Dow Corning 200 and Dow Corning 225 (available from Dow Corning Corp.); Silicone Fluid SF-96 (available from G.E. Silicones); Velvasil™ and Viscasil™ (available from General Electric Co.); Silicone L-45, Silicone L-530, and Silicone L-531 (available from Union Carbide); and Siloxane F-221 and Silicone Fluid SWS-101 (available from SWS Silicones).

Other suitable non-volatile silicone materials that may be employed in antiperspirant compositions manufacturable by the present invention include, but are not limited to, non-volatile silicone emollients such as polyalkylarylsiloxanes, polyestersiloxanes, polyethersiloxane copolymers, polyfluorosiloxanes, polyaminosiloxanes, and combinations thereof. These non-volatile silicone liquid carriers will generally have viscosity values of less than about 100,000 centistokes, less than about 500 centistokes, or from about 1 centistokes to about 200 centistokes or to about 50 centistokes, as measured under ambient conditions.

Silicon-free hydrophobic liquids can be employed alternatively or additionally to liquid silicones. Examples of silicon-free hydrophobic liquids include aliphatic hydrocarbons such as mineral oils, hydrogenated polyisobutane, polydecene, paraffins, isoparaffins, and aliphatic ethers derived from at least one fatty alcohol (e.g., PPG-3 myristeyl ether and PPG-14 butyl ether).

Other hydrophobic liquids include aliphatic or aromatic esters. Exemplary aliphatic esters contain at least one long chain alkyl group, such as ester derived from C1 to C20 alkanols esterified with a C8 to C22 alkanoic acid or C6 to C10 alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate. Exemplary aromatic esters include fatty alkyl benzoates.

Water-immiscible liquids other than those disclosed above may also be employed by the present invention. Further, it is to be understood that the continuous phase may contain hydrophilic materials, so long as the continuous phase overall is water-immiscible.

B. Structurant

Suitable structurants include polyethylene waxes, ozokerite waxes, carnauba waxes, and mixtures thereof. Other suitable structurant materials include N-acyl amino acid amides and esters; for example, N-Lauroyl-L-glutamic acid di-n-butylamide. These materials are described in greater detail in U.S. Pat. No. 3,969,087. 12-hydroxystearic acid and esters and amines of the same represent another class of useful structurants for the antiperspirant compositions of the present invention.

Fiber-forming structurants may also be employed. These materials create a network of fibers or strands that extend throughout the continuous phase to gel the liquids therein. Such materials are generally non-polymeric, being monomers or dimers that can have a molecular weight below about 10,000. Exemplary fiber-forming structurant materials have been reviewed by Terech and Weiss in "Low Molecular Mass Gelators of Organic Liquids and the Properties of their Gels" Chem. Rev 97, 3133-3159 [1997] and by Terech in Chapter 8, "Low-molecular Weight Organogelators" of the book "Specialist Surfactants" edited by I. D. Robb, Blackie Academic Professional, 1997.

Another suitable structurant is a partially or fully esterified cellobiose according the following formula:

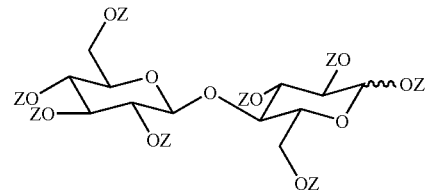

wherein each Z is independently hydrogen or an acyl group of the formula:

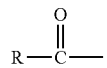

where R denotes a hydrocarbyl group containing from 4 to 22 carbon atoms. It one embodiment, not more than half of the Z groups are hydrogen.

Other suitable thickening or structuring agents for use in the present invention include, but are not limited to, fatty acid gellants, salts of fatty acids, hydroxy fatty acid gellants, esters and amides of fatty acid or hydroxy fatty acid gellants, cholesterolic materials, dibenzylidene alditols, lanolinolic materials, fatty alcohols, and triglycerides.

Suitable thickening or structuring agents can include, but are not limited to, solid salts of fatty acids wherein the fatty acid moiety has from about 12, from about 16 or from about 18 carbon atoms to about 40, to about 22, or about 20 carbon atoms. Suitable salt forming cations for use with these thickening or structuring agents include metal salts such as alkali metals (e.g. sodium and potassium), alkaline earth metals (e.g. magnesium), and aluminum. Preferred are sodium, potassium and aluminum salts. For example, suitable salt forming cations may be selected from the group consisting of sodium stearate, sodium palmitate, potassium stearate, potassium palmitate, sodium myristate, aluminum monostearate, and combinations thereof.

II. Disperse Phase

The disperse phase generally includes water and an aqueous solution of an antiperspirant active. The antiperspirant active for use in compositions that may be made in accordance with the present invention may include any compound, composition or other material having antiperspirant activity. By way of example only, the antiperspirant actives may include astringent metallic salts, especially inorganic and organic salts of aluminum, zirconium and zinc, as well as mixtures thereof. Particular antiperspirant active examples include, but are not limited to, aluminum-containing and/or zirconium-containing salts or materials, such as aluminum halides, aluminum chlorohydrate, aluminum hydroxyhalides, zirconyl oxyhalides, zirconyl hydroxyhalides, and mixtures thereof.

Aluminum salts useful in the present invention include those that conform to the formula:

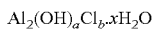

$$Al_2(OH)_aCl_b \cdot xH_2O$$

wherein a is from about 0 to about 5; the sum of a and b is about 6; x is from about 1 to about 8; where a, b, and x may have non-integer values. For example, aluminum chlorohydroxides referred to as "¾ basic chlorohydroxide," wherein a is about 4.5; "⅚ basic chlorohydroxide," wherein a=5; and "⅔ basic chlorohydroxide," wherein a=4 may be used. Processes for preparing aluminum salts are disclosed in U.S. Pat. No. 3,887,692, issued to Gilman on Jun. 3, 1975; U.S. Pat. No. 3,904,741, issued to Jones et al. on Sep. 9, 1975; and U.S. Pat. No. 4,359,456 issued to Gosling et al. on Nov. 16, 1982. A general description of these aluminum salts can also be found in "Antiperspirants and Deodorants, Cosmetic Science and Technology Series" Vol. 20, 2nd edition, edited by Karl Laden. Mixtures of aluminum salts are described in British Patent Specification No. 1,347,950, filed in the name of Shin et al. and published Feb. 24, 1974.

Zirconium salts for use in the present invention include those which conform to the formula:

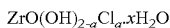

$$ZrO(OH)_{2-a}Cl_a \cdot xH_2O$$

wherein a is from about 0.5 to about 2; x is from about 1 to about 7; where a and x may both have non-integer values. These zirconium salts are described in Belgian Patent No. 825,146, issued to Schmitz on Aug. 4, 1975. Useful to the present invention are zirconium salt complexes that additionally contain aluminum and glycine, commonly known as "ZAG complexes". These complexes contain aluminum chlorohydroxide and zirconyl hydroxy chloride conforming to the above-described formulas. Such ZAG complexes are described in U.S. Pat. No. 4,331,609, issued to Orr on May 25, 1982 and U.S. Pat. No. 4,120,948, issued to Shelton on Oct. 17, 1978.

Compositions that can be manufactured by methods provided herein may additionally or alternatively employ a deodorant active; alternatively meaning that a deodorant active is substituted for an antiperspirant active. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

The disperse phase may optionally contain other polar materials. A representative, nonlimiting list of optional polar materials includes C1 to C20 monohydric alcohols; C2 to C40 dihydric or polyhydric alcohols; alkyl ethers of all such alcohols, e.g., C1-C4 alkyl ethers; polyalkoxylated glycols, e.g., propylene glycols and polyethylene glycols having from 2 to 30 repeating alkoxylate (e.g., ethoxylate or propoxylate) groups and polyglycerols having from 2 to 16 repeating glycerol moieties; and mixtures thereof. More particular exemplary polar materials include propylene glycol, hexylene glycol, dipropylene glycol, tripropylene glycol, glycerin, propylene glycol methyl ether, dipropylene glycol methyl ether, ethanol, n-propanol, n-butanol, t-butanol, 2-methoxyethanol, 2-ethoxyethanol, ethylene glycol, isopropanol, isobutanol, 1,4-butylene glycol, 2,3-butylene glycol, trimethylene glycol, 1,3-butanediol, 1,4,-butanediol, propylene glycol monoisostearate, PPG-3 myristyl ether, PEG-4 (also known as PEG-200), PEG-8 (also known as PEG-400), 1,2, pentanediol, PPG-14 butylether, dimethyl isosorbide, 1,2 hexanediol and combinations thereof. It is to be understood that polar materials other than those listed above may also be employed in the antiperspirant compositions described herein.

III. Surfactants

Emulsifying surfactants are employed in the antiperspirant compositions to facilitate the formation of a stable emulsion containing the above-described continuous phase and disperse phase. The emulsifying surfactants may be anionic, cationic, zwitterionic and/or nonionic surfactants. Nonionic surfactants are preferred in the current invention. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Emulsifiers are frequently classified by HLB value. It is desirable, although not required, to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. C16 to C18 alcohols ethoxylated with 10 to 25 ethylene oxide residues) and PEG-15-25 stearate or distearate. Other suitable examples include C10-C20 fatty acid mono, di or tri-glycerides. Further examples include C18-C22 fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from C14 to C22 and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers also include C1 to C12 alkyl groups as functional groups. Examples of suitable surfactants include DC5225 and DC 5200 (from Dow Corning), Abil EM 90 and EM 97 (from Gold Schmidt) and KF 6026, KF 6028, KF 6038 (from Shinetsu Silicones).

The skilled artisan should appreciate that other emulsifying surfactants than those described above may also be used in antiperspirant compositions described herein.

IV. Formation of the Emulsion

The continuous phase, disperse phase, and emulsifying surfactant are combined and then mixed or otherwise agitated sufficiently to form an emulsion. Typically, the disperse phase is added slowing to the continuous phase while the continuous phase is being vigorously agitated with a mixing system. The skilled artisan should appreciate the degree of mixing needed based on the desired phase ratio of the emulsion, its resulting viscosity and the desired batch size. The resulting emulsion can be further processed to create a consistent droplet size within the emulsion; for example, the emulsion may be processed by a mill to reduce droplet size and/or improve droplet size uniformity. Preferably, the emulsion is processed so that the entire batch experiences an equivalent amount of shear. A single-phase inline mill is one preferred apparatus for the additional, optional processing.

V. Optional Ingredients

Antiperspirant compositions of the present invention may include one or more fragrance/perfume materials. In one preferred embodiment, the composition includes a fragrance material comprising a plurality of different perfume raw materials. Typical perfume levels in the present invention are 0.25 to 5%. Nonlimiting examples of fragrance materials include any known fragrances in the art or any otherwise effective fragrance materials. Typical fragrances are described in Arctander, "Perfume and Flavour Chemicals (Aroma Chemicals)", Vol. I and II (1969) and Arctander, "Perfume and Flavour Materials of Natural Origin" (1960). U.S. Pat. No. 4,322,308, issued to Hooper et al., Mar. 30, 1982 and U.S. Pat. No. 4,304,679, issued to Hooper et al., Dec. 8, 1981 disclose suitable fragrance materials including, but not limited to, volatile phenolic substances (such as iso-amyl salicylate, benzyl salicylate, and thyme oil red), essence oils (such as geranium oil, patchouli oil, and petitgrain oil), citrus oils, extracts and resins (such as benzoin siam resinoid and opoponax resinoid), "synthetic" oils (such as Bergamot™ 37 and Bergamot™ 430, Geranium™ 76 and Pomeransol™ 314), aldehydes and ketones (such as B-methyl naphthyl ketone, p-t-butyl-A-methyl hydrocinnamic aldehyde and p-t-amyl cyclohexanone), polycyclic compounds (such as coumarin and beta-naphthyl methyl ether), esters (such as diethyl phthalate, phenylethyl phenylacetate, non-anolide 1:4).

Suitable fragrance materials may also include esters and essential oils derived from floral materials and fruits, citrus oils, absolutes, aldehydes, resinoides, musk and other animal notes (e.g., natural isolates of civet, castoreum and musk), balsamic, and alcohols (such as dimyrcetol, phenylethyl alcohol and tetrahydromuguol). For example, the antiperspirant compositions may comprise fragrances selected from the group consisting of decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, amyl-cyclohexanone, and mixtures thereof. Fragrance materials other than those listed above may also be employed.

The antiperspirant compositions can also include residue-masking agents to reduce the appearance of white residue arising from the antiperspirant active and structurant employed in the product. These masking agents can be incorporated into either the continuous or disperse phased depending on their water solubility. Exemplary residue-masking agents include isostearyl isostearate, glycereth-7-benzoate, C12-C15 alkyl benzoate, octyldodecyl benzoate, isostearyl lactate, isostearyl palmitate, benzyl laurate, laureth 4, laureth 7, oleth 2, PEG 4, PEG 12, isopropyl myristate isopropyl palmate, butyl stearate, polyethylene glycol methyl ethers, PPG 2 ceteareth 9, PPG 2 isodeceth 12, PPG 5 butyl ether, PPG 14 butyl ether, PPG 15 butyl ether, PPG 53 butyl ether, octyldodecanol, polydecene, mineral oil, petrolatum, phenyltrimethicone, dimethicone copolyol, and mixtures thereof. One preferred concentration level of the optional residue-masking agent is from about 3% to about 10%, by weight of the composition. But other concentration levels may also be used.

Antiperspirant compositions of the present invention may employ one or more additional ingredients. Nonlimiting examples of such optional ingredients include, but are not limited to, pH buffering agents, additional malodor controlling agents, emollients, humectants, soothing agents, dyes and pigments, medicaments, baking soda and related materials, preservatives, and soothing agents such as aloe vera, allantoin, D-panthenol, pantothenic acid derivatives (e.g., those disclosed in U.S. Pat. No. 6,495,149), avocado oil and other vegetative oils, and lichen extract.

VI. Product Clarity

Antiperspirant products made in accordance with the present invention may be opaque, translucent, or transparent. In one preferred embodiment, a 1 cm thick portion/sample of the antiperspirant product has at least 1% light transmission at 580 nm and 22° C. The following test method can be used to determine light transmission exhibited by the antiperspirant products and/or portions thereof. While still mobile, pour a sample of an antiperspirant composition into a 4.5 ml cuvette made of polymethylmethacrylate and allow to cool to a temperature of 22° C. Such a cuvette gives a 1 cm thickness of the composition. Measurement is to be carried out at 580 nm, with an identical but empty cuvette in the reference beam of a dual-beam spectrophotometer, after the sample has been held for 24 hours.

VII. Methods for Manufacturing Antiperspirant Compositions

The description and appended claims include a listing of steps with either letter or numerical designations associated with the individual steps. It is to be understood that although they may, the methods and steps do not necessarily need to be performed in the order as shown in the figures, order of listing, or in accordance with their associated designations; for example, a step (d) may be performed before or after a step (b). Furthermore, although steps are listed individually, some steps may be performed simultaneously with other steps. Alternatively, the steps are all performed sequentially. Timing of the steps can vary. Also, there may or may not be delays between steps. And the methods described herein may include other steps than those explicitly listed and/or recited in the appended claims.

A. First Exemplary Embodiment

Referring to FIG. 1, a first exemplary method is shown wherein a disperse aqueous phase and a continuous water-immiscible phase are provided. The disperse phase contains an antiperspirant active in an aqueous solution. The continuous phase block includes an emulsifying surfactant, the structurant and at least a portion of the other ingredients that ultimately end up in the product continuous phase. Each of the phases are heated, the continuous phase being heated to a temperature sufficient to at least partially dissolve the structurant, and the aqueous phase preferably being heated to a similar temperature (e.g., within 10° C.) to that of the continuous phase. While mixing the heated continuous phase, the heated disperse phase is introduced into the continuous phase. The speed of mixing can be increased if needed to form an acceptable emulsion. Moreover, the heated emulsion can be milled during or after the addition of the dispersed phase to assure formation of a uniform particle size. The emulsion can then be transferred into a suitable container (e.g., a dispenser) while it is still in a mobile condition, which includes being at a similar temperature or a lower temperature than when the two phases were combined. The emulsion may be cooled through an active step—that is, for example, via exposure to forced air, passage through a cooled environment or the like. Otherwise the emulsion is allowed to cool simply through radiation and/or conductive heat transfer away from the container.

A significant percentage of the volatile ingredients—for example, water and a volatile water-immiscible liquid—can be lost during manufacture due to the relatively high heat levels associated with the methods, particularly when the methods are used for commercial-scale manufacturing (e.g., batch weights of at least about 5 Kg, 10 Kg, 20 Kg, or higher). Not only does the loss of these materials increase raw material costs, but special equipment may be required to recover volatilized materials so that worker and environment health are addressed. Thus, in accordance with preferred embodiments of the present invention, the residence time of the aqueous phase and/or the emulsion at temperatures of greater than or equal to about 60° C. are limited to less than about two hours, one and half hours, one hour, 30 minutes, or 15 minutes. Other high temperature residence time limitations of the aqueous phase and/or emulsion include temperatures of greater than or equal to about 55° C. for less than about two hours, greater than or equal to about 50° C. for less than about two hours, and greater than or equal to about 80° C. for less than about 15 minutes.

B. Second Exemplary Embodiment

Figure 2:
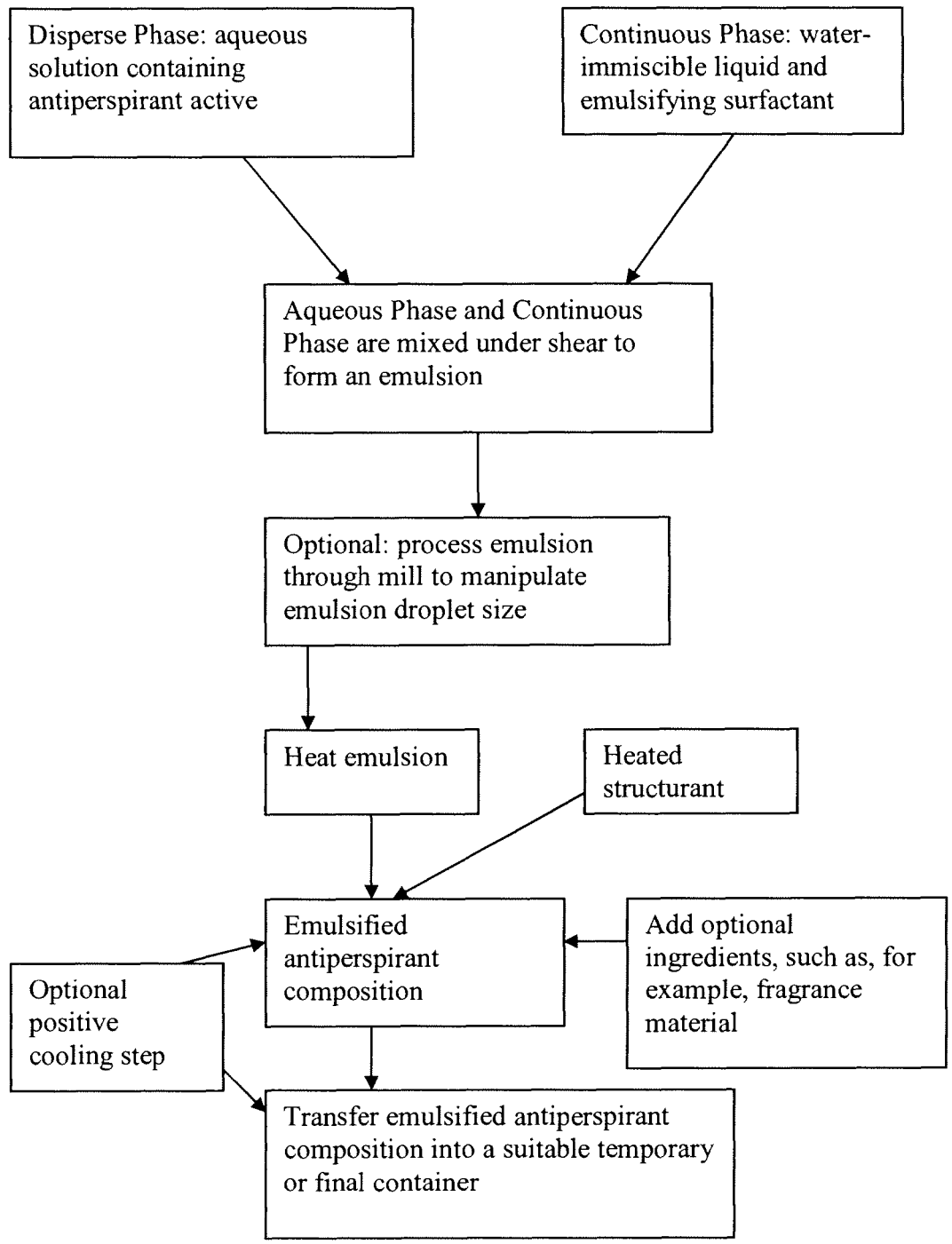
FIG. 2 is a schematic of a second exemplary method for making antiperspirant products.

Referring to FIG. 2, a second exemplary method is shown wherein a disperse aqueous phase and a continuous water-immiscible phase are provided. The disperse phase contains an antiperspirant active in an aqueous solution. The continuous phase contains one or more water-immiscible liquids and an emulsifying surfactant. The two phases are combined under shear to form an emulsion. As shown in FIG. 2, the emulsion may be processed further, for example, via a mill to manipulate the emulsion droplet size or size distribution—this optional additional processing may apply to all of the method embodiments provided herein. The emulsion is then heated. A structurant material is heated in a separate container and then added to the heated emulsion to form an emulsified antiperspirant composition. The structurant is preferably heated to a temperature sufficient to at least partially dissolve the structurant. More preferably the temperature is sufficient to completely melt the structurants. The emulsion is preferably heated to a temperature similar to the temperature of the structurant. For example, the emulsion can be heated to a temperature within about 10° C. of the heated structurants.

Other ingredients may be added to the emulsified antiperspirant composition. For example, fragrance materials, residue-masking agents, or other hydrophobic/hydrophilic materials can be added to define the final antiperspirant product. As with the first exemplary embodiment described above, the emulsified antiperspirant composition may be actively cooled and/or simply allowed to cool, whereby the product hardens to the designed level of solid form. The emulsified antiperspirant composition is transferred into a suitable temporary or final container (i.e., a dispensing package or portion thereof (e.g., a "barrel")).

In one preferred embodiment, the emulsified antiperspirant composition is transferred into the temporary or final container within a relatively short period of time—within 2 hours, 1 hour, 45 minutes, 30 minutes, 15 minutes, 10 minutes, or 5 minutes of initiating the step of heating the emulsion. In another preferred embodiment, the emulsified antiperspirant composition is transitioned to a temperature below about 60° C. (e.g., with active and/or passive cooling) within a relatively short period of time—within 2 hours, 1 hour, 45 minutes, 30 minutes, 15 minutes, 10 minutes, or 5 minutes of completing the step of heating the emulsion. The antiperspirant composition during this transition time may already be located in a final container/package or portion thereof, may be being placed into its final container or portion thereof, or may not yet be transferred into the final package or portion thereof.

C. Third Exemplary Embodiment

Figure 3:
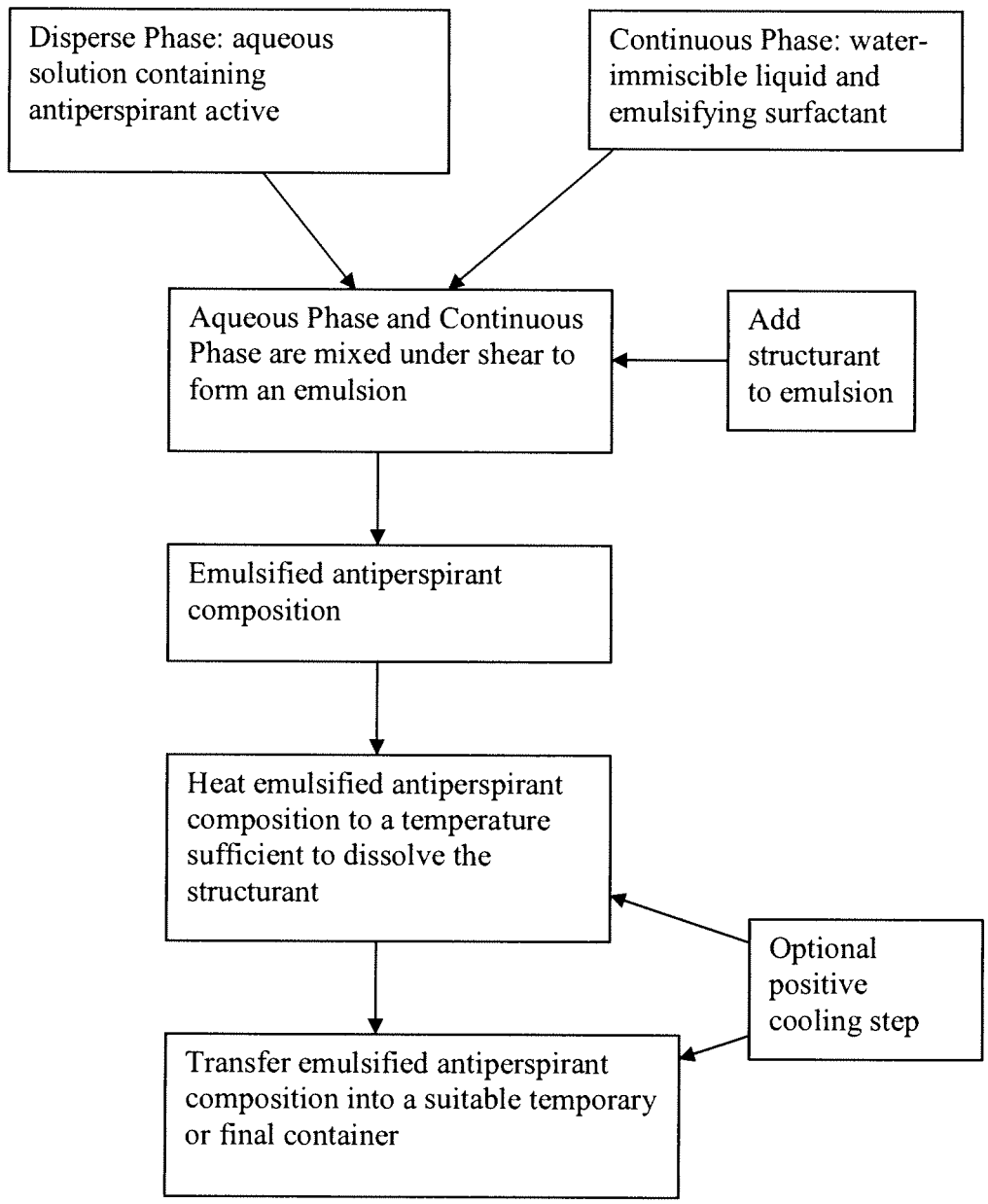
FIG. 3 is a schematic of a third exemplary method for making antiperspirant products.

Referring to FIG. 3, a third exemplary method is shown wherein a disperse aqueous phase and a continuous water-immiscible phase are provided. The disperse phase contains an antiperspirant active in an aqueous solution. The continuous phase contains one or more water-immiscible liquids and an emulsifying surfactant. The two phases are combined under shear to form an emulsion. A structurant material is added to the emulsion to form an emulsified antiperspirant composition. During this step, the structurant material and/or emulsion may be unheated or heated; preferably, both the structurant material and emulsion are at room temperature when the two are combined. The emulsified antiperspirant composition is subsequently heated to a temperature sufficient to at least partially dissolve the structurant.

Other ingredients may be added to the emulsified antiperspirant composition. For example, fragrance materials, residue-masking agents, or other hydrophobic/hydrophilic materials can be added to define the final antiperspirant product. As with the first and second exemplary embodiments described above, the emulsified antiperspirant composition may be actively cooled and/or simply allowed to cool, whereby the product hardens to the designed level of solid form. The emulsified antiperspirant composition is transferred into a suitable temporary or final container (i.e., a dispensing package or portion thereof (e.g., a "barrel")).

In one preferred embodiment, the emulsified antiperspirant composition is transferred into the temporary or final container within a relatively short period of time—within 2 hours, 1 hour, 45 minutes, 30 minutes, 15 minutes, 10 minutes, or 5 minutes of initiating the step of heating the emulsion. In another preferred embodiment, the emulsified antiperspirant composition is transitioned to a temperature below about 60° C. (e.g., with active and/or passive cooling) within a relatively short period of time—within 2 hours, 1 hour, 45 minutes, 30 minutes, 15 minutes, 10 minutes, or 5 minutes of completing the step of heating the emulsion. The antiperspirant composition during this transition time may already be located in a final container/package or portion thereof, may be being placed into its final container or portion thereof, or may not yet be transferred into the final package or portion thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an emulsified antiperspirant product comprising a continuous phase that includes a water-immiscible liquid and a disperse aqueous phase comprising an antiperspirant active, the method comprising the steps of:
    (a) providing a water-immiscible liquid;
    (b) providing volatile aqueous solution comprising an antiperspirant active;
    (c) combining the water-immiscible liquid and the aqueous solution to form an emulsion comprising a continuous phase including the water-immiscible liquid and a disperse phase including the aqueous solution;
    (d) heating the emulsion to a temperature between about 60° C. and about 110° C. for only about 15 minutes to less than about 2 hours to reduce the loss of the volatile aqueous solution;
    (e) heating a structurant separate from the emulsion, to a temperature so that it is at least partially dissolved;
    (f) combining the heated emulsion of step (d) and the at least partially dissolved structurant of step (e) to form an emulsified antiperspirant composition having a batch weight of about 20 kg or higher; and
    (g) transferring a portion of the emulsified antiperspirant composition into a dispensing container.

2. The method of claim 1, wherein the water-immiscible liquid is a volatile silicone and the structurant is selected from the group consisting of a polyethylene wax, an ozokerite wax, a carnauba wax, a fibre-forming structurant material, and mixtures thereof.

3. The method of claim 1, wherein the emulsion is heated for only about 15 minutes to about 1.5 hours.

4. The method of claim 1, wherein the emulsion is heated for only about 15 minutes to about 30 minutes.

5. The method of claim 1, wherein step e) further comprises heating the structurant in a container separate from heated emulsion and further comprises heating the structurant to a temperature within about 10° C. of the temperature of the heated emulsion.

6. The method of claim 1, further comprising a step of actively cooling the emulsified antiperspirant composition after it is transferred into the dispensing container.

7. A method for making an emulsified antiperspirant product comprising a continuous phase that includes a water-immiscible liquid and a disperse aqueous phase comprising an antiperspirant active, the method comprising the steps of:
    (a) providing a water-immiscible liquid;
    (b) providing a volatile aqueous solution comprising an antiperspirant active and water;
    (c) combining the water-immiscible liquid and the aqueous solution to form an emulsion comprising a continuous phase including the water-immiscible liquid and a disperse phase including the aqueous solution;
    (d) heating the emulsion to a temperature between about 60° C. and about 110° C.;
    (e) providing a structurant separate from the emulsion;
    (f) combining the heated emulsion of step (d) and the structurant of step (e) to form an emulsified antiperspirant composition, wherein the batch weight of the emulsified antiperspirant composition is greater than 20 kg;
    (g) transferring a portion of the emulsified antiperspirant composition into a dispensing container to form an antiperspirant product;
    (h) cooling the emulsified antiperspirant composition; and
    wherein the emulsion of step (d) is heated for only about 15 minutes to less than about 2 hours to reduce the loss of the volatile aqueous solution.

8. The method of claim 7, wherein the water-immiscible liquid is a volatile silicone and the structurant is selected from the group consisting of a polyethylene wax, an ozokerite wax, a carnauba wax, a fibre-forming structurant material, and mixtures thereof.

9. The method of claim 7, wherein the emulsion is heated for only about 15 minutes to about 1.5 hours.

10. The method of claim 7, wherein the emulsion is heated for only about 15 minutes to about 30 minutes.

11. The method of claim 7, wherein step e) further comprises heating the structurant to a temperature sufficient to at least partially dissolve the structurant, in a container separate from heated emulsion and further comprises heating the structurant to a temperature within about 10° C. of the temperature of the heated emulsion.

12. A method for making an emulsified antiperspirant product comprising a continuous phase that includes a water-immiscible liquid and a disperse aqueous phase comprising an antiperspirant active, the method comprising the steps of:
   (a) providing a water-immiscible liquid;
   (b) providing a volatile aqueous solution comprising an antiperspirant active and water;
   (c) combining the water-immiscible liquid and the aqueous solution to form an emulsion comprising a continuous phase including the water-immiscible liquid and a disperse phase including the aqueous solution;
   (d) heating the emulsion to a temperature between about 60° C. and about 110° C. for only about 15 minutes to less than about 2 hours to reduce the loss of the volatile aqueous solution;
   (e) providing a structurant separate from the emulsion
   (f) combining the heated emulsion of step (d) and the structurant of step (e) to form an emulsified antiperspirant composition having a batch weight of about 20 kg or higher; and
   (g) transferring a portion of the emulsified antiperspirant composition into a dispensing container.

13. The method of claim 12, wherein the water-immiscible liquid is a volatile silicone and the structurant is selected from the group consisting of a polyethylene wax, an ozokerite wax, a carnauba wax, a fibre-forming structurant material, and mixtures thereof.

14. The method of claim 12, wherein the emulsion is heated for only about 15 minutes to about 1.5 hours.

15. The method of claim 12, wherein the emulsion is heated for only about 15 minutes to about 30 minutes.

16. The method of claim 12, wherein step e) further comprises heating the structurant in a container separate from heated emulsion and further comprises heating the structurant to a temperature within about 10° C. of the temperature of the heated emulsion.

* * * * *